United States Patent [19]
Herr

[11] Patent Number: 5,458,114
[45] Date of Patent: Oct. 17, 1995

[54] CONTRACEPTIVE PENILE CAP

[76] Inventor: Jan E. Herr, P.O. Box 15044, San Diego, Calif. 92175

[21] Appl. No.: 421,750

[22] Filed: Apr. 14, 1995

[51] Int. Cl.⁶ ..................................................... A61F 6/02
[52] U.S. Cl. ............................ 128/842; 128/844; 128/918
[58] Field of Search .................................... 128/842, 844, 128/918; 604/330, 347–353

[56] References Cited

U.S. PATENT DOCUMENTS

| | | | |
|---|---|---|---|
| 3,037,508 | 6/1962 | Friedman | 128/844 |
| 3,677,225 | 7/1972 | Czirely | 128/132 |
| 3,683,904 | 8/1972 | Forster | 128/842 |
| 4,821,742 | 4/1989 | Phelps | 128/842 |
| 4,869,269 | 9/1989 | Sharkan | 128/844 |
| 4,917,113 | 4/1990 | Conway et al. | 128/844 |
| 4,955,392 | 9/1990 | Sorkin | 128/918 |
| 5,102,405 | 4/1992 | Conway et al. | 604/352 |

Primary Examiner—Michael A. Brown
Attorney, Agent, or Firm—Henri J. A. Charmasson; John D. Buchaca

[57] ABSTRACT

A new and useful contraceptive and prophylactic attachment having a dome shaped bowl which conforms to the shape of a portion of the penile glans surrounding the urethral orifice. The bowl has an aperture overlying the orifice which leads into a collapsed bladder contained within a protective retaining structure. During ejaculation, semen flows through the aperture into the bladder expanding it and causing it to extrude itself through an expandable outlet in the retaining structure. As a penile cap or micro-condom, the shape of the bowl and a layer of medical grade adhesive forms a leak-free seal between the attachment and the penis. The sensitive corona of the glans is left exposed.

13 Claims, 2 Drawing Sheets

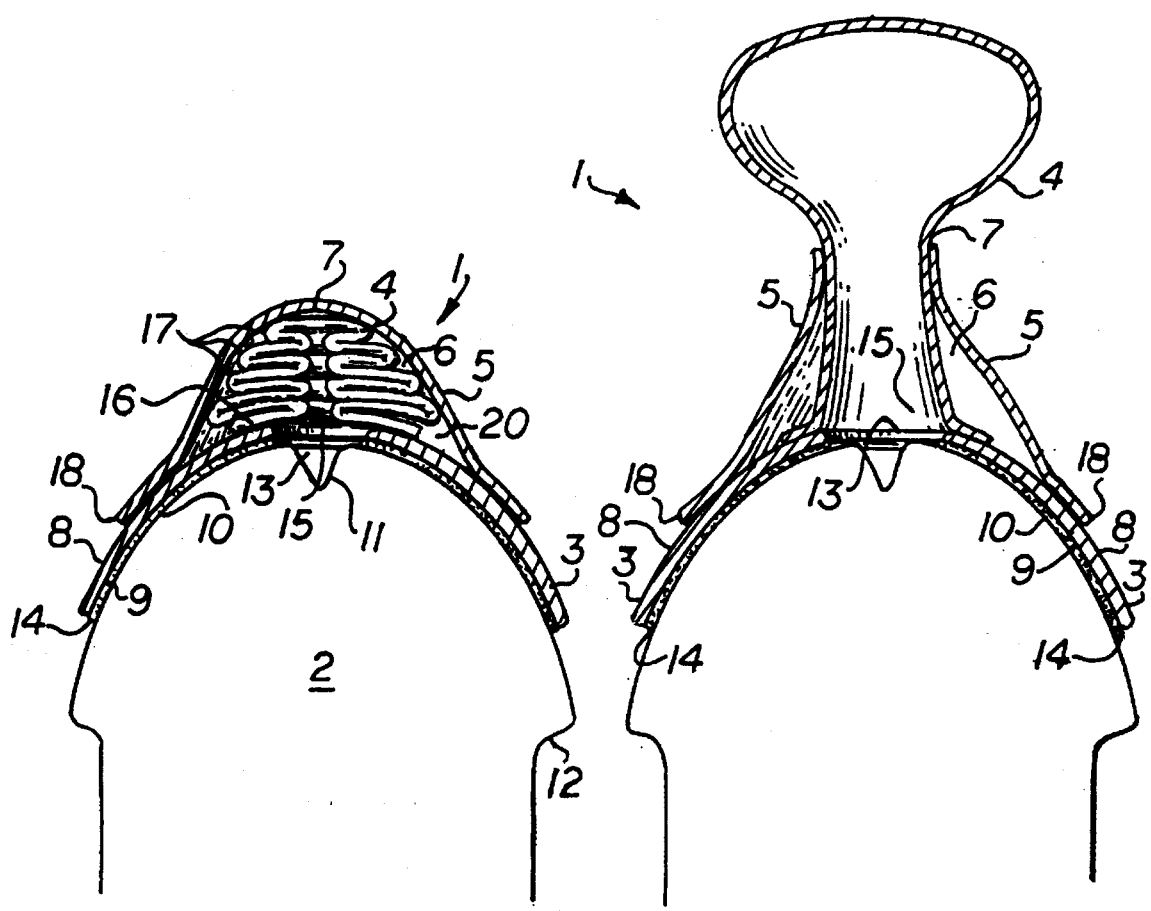
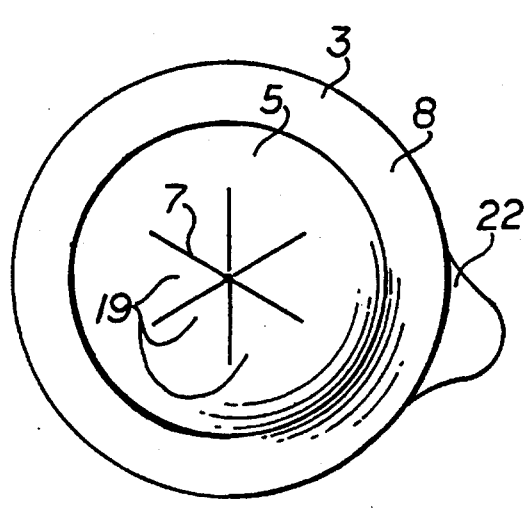
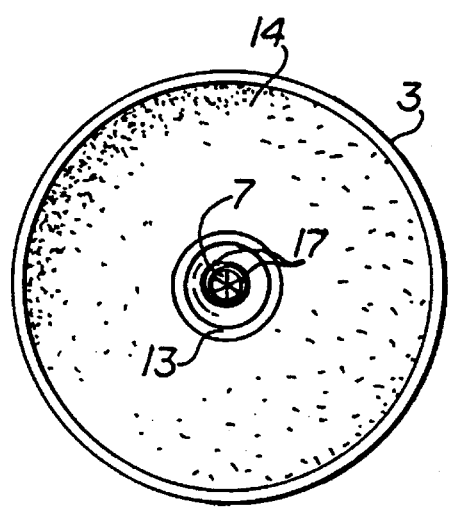
FIG. 1
FIG. 2
FIG. 3
FIG. 4

CONTRACEPTIVE PENILE CAP

FIELD OF THE INVENTION

This invention relates to contraceptive and prophylactic devices for preventing pregnancy and the transmission of sexually transmitted diseases (STDs) during sexual intercourse, and more particularly to condoms and so-called micro-condoms or penile caps.

BACKGROUND OF THE INVENTION

The conventional contraceptive-prophylactic condom is designed to cover not only the penile glans but a major portion of the penile shaft as well. It is typically applied in an initially roll-up condition and is unrolled to extend over almost the entire length of the tumescent male organ. It is retained in position largely by the friction between its inner wall and the outer surface of the penile shaft. An objection to contraceptive devices of this type is that the pull-down hood which covers the penile shaft interferes with stimulation. Also, it may slip off when the penis assumes a flaccid condition after ejaculation. This slippage may result in seminal fluid accidentally entering the vaginal passage. Another objection to the use of conventional condoms is that their thinness tends to allow them to tear or leak during use, thereby permitting seminal fluid to enter the vaginal passage. The leakage problem can be diminished by manufacturing the condom of thicker material, but such a method will further lower the level of stimulation afforded the user.

Attempts have been made to solve the leakage problem by utilizing an adhesive material to secure a miniature condom or contraceptive cap to the tip or glans of the male sex organ. U.S. Pat. No. 3,677,225, for example, discloses a micro-condom or penile cap which covers the glans rather than the greater part of the penis. Although this device is targeted toward increased user stimulation, it could very easily become dislodged during the sexual act because its loose and unprotected seminal reservoir would be pulled upon by the movement of the glans against the wall of the vaginal canal.

U.S. Pat. No. 4,869,269 discloses a micro-condom or penile cap which is formed more closely to the shape of the glans, thereby reducing leakage. Because it is made of more rigid material, it reduces the problem of the seminal reservoir being caught between the glans and the vaginal wall and being thereby dislodged. This device provides a seminal reservoir, however, that is much too large, rigid, and projecting for the comfort of the user's partner.

SUMMARY OF THE INVENTION

The primary and secondary objects of the invention are to provide a contraceptive and prophylactic device which reduces the probability of leakage and increases the pleasure of both the user and his partner over that afforded by a conventional condom or penile cap.

It is a further object of the invention is to provide a device which is sufficiently small, soft, and compact as to minimize the discomfort to the user's partner and significantly reduce the probability of its being dislodged during coitus, which can occur with presently available micro-condoms or penile caps.

These and other objects are achieved through a contraceptive prophylactic attachment which is installed on the penis to act as a barrier to the exchange of bodily fluids during sexual activity. The attachment comprises a dome-shaped bowl which conforms to the shape of a portion of the penile glans surrounding the urethral orifice. The bowl has an aperture overlying the orifice which leads into a collapsed bladder contained within a protective retaining structure. During ejaculation, semen flows through the aperture into the bladder, thereby expanding it and causing it to extrude itself through an expandable outlet in the retaining structure.

In its penile cap or micro-condom embodiment, the shape of the bowl and a layer of medical grade adhesive forms a leak-free seal between the attachment and the penis. The invention leaves exposed the corona (the ridge around the circumference of the glans), which is one of the most sensitive parts of the male sexual organ. This eliminates the need for the roll-down hood of conventional full-size condoms and the rigid and projecting seminal reservoir of previously designed miniature condoms and penile caps.

BRIEF DESCRIPTION OF THE DRAWING

FIG. 1 is a diagrammatic cross sectional side view of an installed penile cap according to the invention;

FIG. 2 is a diagrammatic cross sectional side view of the installed penile cap of FIG. 1, after extrusion of the bladder;

FIG. 3 is a diagrammatic top view of the penile cap according to the invention;

FIG. 4 is a diagrammatic bottom view of the penile cap of FIG. 3 with the protective cover removed;

DESCRIPTION OF THE PREFERRED EMBODIMENT OF THE INVENTION

Figure 5:
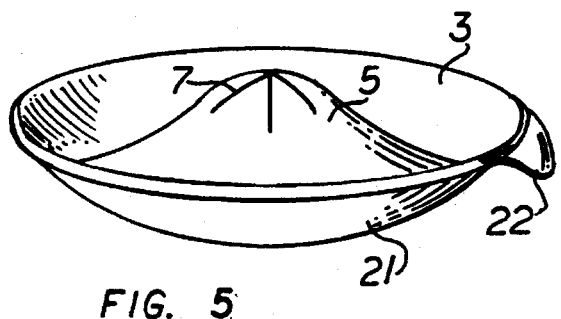
FIG. 5 is a diagrammatic perspective view of the penile cap according to the invention prior to installation.

Referring now to the drawing, FIGS. 1–6 show the contraceptive prophylactic penile attachment 1, in the form of a micro-condom or penile cap, according to the invention. In FIGS. 1 and 2, the attachment is shown installed on a penis 2. The attachment comprises an adhering bowl structure 3, a seminal reservoir or bladder 4, and a retaining structure or envelope 5 all made from pliable sheet material.

Prior to ejaculation, FIG. 1 shows that the bladder 4 remains in a collapsed state and is retained within a chamber 6 formed inside the envelope 5, above the bowl. An outlet 7 formed in the top of the envelope is in a closed position. After ejaculation, FIG. 2 shows that the bladder 4 has been extruded through the outlet which has been forced into its open position by the pressure of the enlarged bladder.

These major components, the bowl, bladder and envelope may be manufactured separately, then bonded to each other. Alternatively, various combinations of these components or all these components may be manufactured as a single unit which does not require bonding.

The bowl 3 is generally hemispherical in shape having an upper surface 8 and a lower arcuate surface 9 which is sized and dimensioned to conform with the upper portion of the glans 10 surrounding the urethral orifice 11. The diameter of the bowl is preferably between about five-eights and seven-eighths of an inch which is generally small enough to leave exposed the sensitive corona 12 portion of the glans.

A substantially central portion of the bowl 3 is perforated with a generally circular aperture 13 which will overlie the urethral orifice 11. The preferred size of the aperture is about three-eights of an inch in diameter. The aperture is made generally circular to allow installation of the cap without regard to its rotational orientation atop the penis. However, any shape aperture which comfortably allows the passage of semen to the inside of the bladder is acceptable. Similarly, the term "substantially central portion" is used to allow for more detailed designs of the bowl structure and aperture location which more closely conforms to the anatomical shape of the glans.

The bowl 3 is made from pliable sheet material such as natural or synthetic rubber such as latex rubber, soft plastic or other soft flexible material currently available in the art. The bowl is of approximately uniform thickness, preferably being between about 0.001 inch and about 0.008 inch, and most preferably about 0.005 inch. This thickness may vary depending upon the type of material used, but should be sufficient to resist tearing during the installation and use of the attachment. It is anticipated that as the condom industry continues to develop thinner stronger sheet material, this material will be applicable to the present invention.

The lower surface 9 of the bowl is coated with a substantially uniform layer of pressure-sensitive adhesive 14 as a means for securing the attachment to the penis. The adhesive layer functions similarly in manner to that of a commercial bandage. The layer preferably covers the entire area of contact between the bowl and the penile glans. Although a uniform layer of medical grade adhesive is the preferred approach, other adhesives or means for securing the attachment such as suction or friction from elastic structures may be adequate without departing from the invention.

The adhesive layer 14 may be imparted onto the attachment through any commercially feasible method such as through the use of medical-grade adhesive transfer film. Examples of such transfer films appropriate for this purpose are Fitchburg 545, 591, 594, and 597 free films coated onto a thermoformable polyester liner. Alternatively, the adhesive may be sprayed onto the inner surface of the lower surface of the bowl. A suitable adhesive for spraying is Monsanto Gelva Acrylic Water-based Medical Grade Adhesive 2222. A suitable apparatus for spraying is the Nordson Airless Spray System.

The seminal reservoir of the attachment is formed by a bladder 4 having a single open end or opening 15. The bladder is made of pliable sheet material such as natural or synthetic rubber such as latex rubber, soft plastic or other soft flexible material currently available in the art. The bladder has a thickness preferably between 0.001 and 0.008 of an inch, and most preferably about 0.005 of an inch. However, this thickness may vary depending on the material used, but should be sufficient to render it fully impermeable to the constituents of seminal fluid, including possible disease agents such as viruses. As stated above, it is likely that future improvements in pliable sheet material for use in condoms will be applicable to the present invention. When expanded, the bladder's volume is approximately three-fourths of a fluid ounce.

The substantially circular open end 15 of the bladder is about three-eights of an inch in diameter, and is centered over the aperture 13 through the bowl 3. The bladder may be formed having a circumferential edge 16 which is permanently bonded to the upper surface 8 of the bowl. Alternatively, the bladder may be manufactured connected to the bowl as a single unit. Either way, there exist means for exposing the opening to the urethral orifice.

Until it receives semen, the bladder 4 remains in a collapsed state. Preferably, the bladder is collapsed by forming a plurality of folds 17. The bladder is folded or collapsed in such a way as to allow expansion and extrusion of the bladder through the outlet when semen is ejaculated into the bladder. In its collapsed state the bladder is compressed and covered by the envelope retaining structure 5, thereby preventing the bladder from being dislodged during sexual activity.

The envelope 5 is generally dome-shaped and is preferably in an ogive or rounded parabolic form approximately one-half inch in diameter and one-half inch high. The pliable envelope is made from latex rubber, soft plastic or other flexible sheet material. However, it should preferably be relatively less pliable than the bladder. The envelope may be formed having a circumferential edge 18 which is permanently bonded to the upper surface 8 of the bowl. Alternatively, the envelope may be manufactured connected to the bowl as a single unit using processes well known in the art. Either way, the envelope is connected to the upper surface of the bowl.

As shown in FIG. 3, the center of the outer surface of the envelope 5 is perforated by the outlet 7 in a star-like pattern so as to form a plurality of interrelating leaves or flaps 19 whose edges form the outlet in the closed position. The flexible leaves are biased to remain in the closed position until forced outward into an open position by the pressure of the extruding bladder.

In the present embodiment, the means which allow the extrusion of the bladder through the envelope comprise the outlet formed by cuts extending radially from the apex of the upper arcuate portion of the envelope in a star-like pattern. However, other means common in the art such as a perforation which forms a single flap such as a trap-door style opening are acceptable.

To facilitate extrusion, an amount of lubricant may be present within the folds 17 of the outer surface of the bladder 4 inside the envelope 5. If a slight space 20 is formed between the bladder and the envelope, lubricant may be present there exclusively or in addition to lubricant within the bladder folds.

Figure 6:
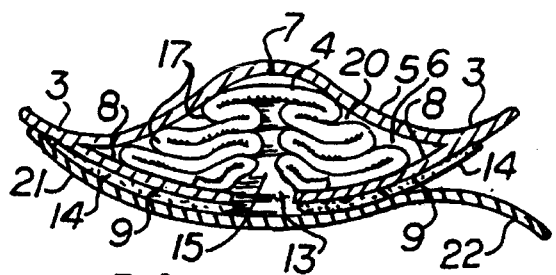
FIG. 6 is a diagrammatic cross sectional side view of the penile cap showing the removable protective cover.

FIG. 5 and 6 show that the penile cap may be distributed in an inverted configuration where the lower surface 9 of the bowl is convex. This facilitates installing the cap on the penis. A removable protective cover 21 is shown in contact with what would be exposed portions of the adhesive layer 14. The cover is generally cup-shaped having a size equal to or greater than that of the bowl. The cover preferably has a pull tab 22 which extends beyond an edge of the bowl 3. The cover is preferably made from a thin sheet of paper, rubber, plastic or similar material which is easily peeled away from the adhesive layer prior to installation. The cover prevents the adhesive from drying out or becoming contaminated with foreign matter much in the same manner as a paper or plastic shield protects a commercial bandage. It also prevents the inadvertent securing of the cap to incidental structures prior to use. The removable protective cover also provides structural support for bowl prior to installation.

Like condoms, the function of the present invention is to receive and contain the seminal fluid released by the male during sexual orgasm. This invention has, however, significant advantages over both standard condoms and previously designed micro-condoms or penile caps.

The first advantage of the invention is that it covers neither the penile shaft nor the major part of the glans. It thus allows significantly greater stimulation of the user during sexual activity. This increased and more natural stimulation as compared with that afforded by a condom increases its desirability as a contraceptive and prophylactic means.

The second advantage of the invention is that, because it covers neither the corona nor the penile shaft, its seminal reservoir can be made of substantially thicker material. This increased thickness consequently strengthens the said material against tearing or otherwise permitting seminal fluid to enter the vaginal passage.

The third advantage of the invention is the small, soft, and minimally projecting enclosure of the seminal reservoir which greatly reduces the possibility of discomfort to the user's partner caused by the much larger, rigid, and projecting seminal reservoir of currently micro-condoms or penile caps.

The fourth advantage of the invention is that its smaller, softer, and less projecting seminal reservoir enclosure appreciably reduces the probability of the contraceptive penile cap being dislodged during sexual activity.

Figure 7:
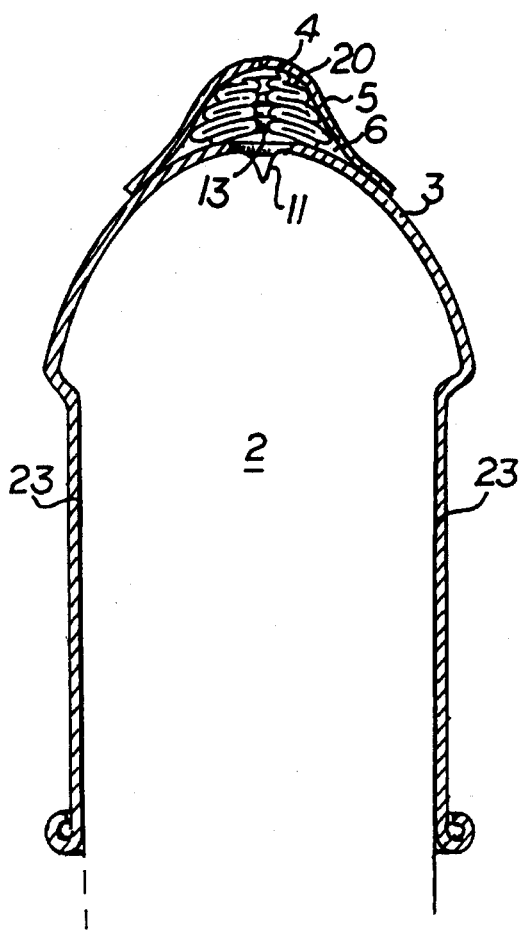
FIG. 7 is a diagrammatic cross sectional side view of an installed full-size condom according to the invention.

Although the preferred embodiment of the invention is directed toward micro-condom type penile caps, the invention is also applicable to more traditional condom designs as shown in FIG. 7. Under this approach, adhesives may or may not be used. The friction of the walls 23 of the full size condom provide the means for securing the attachment 1 to the penis 2. The advantage here is that the extended wall 23 of the traditional condom may be made thinner because the risk of semen escaping through a hole in the wall is reduced by the addition of the inventive structures. A thinner walled full size condom would offer greater pleasure to the user. Full size condoms may be preferred in situations where STDs may be transmitted through lesions or abrasions on the shaft of the penis. Other advantages of full size condoms such as automatic lubrication would still be available with the addition of the invention's structures.

While the preferred embodiments of the invention have been described, modifications can be made and other embodiments may be devised without departing from the spirit of the invention and the scope of the appended claims.

What is claimed is:

1. A contraceptive, prophylactic penile attachment which comprises:

a retaining structure having an expandable outlet;

a collapsed pliable bladder contained within said structure, said bladder having a single opening;

wherein said outlet is sized and dimensioned to allow extrusion of a portion of said bladder therethrough;

means for exposing said opening to the urethral orifice of a penis; and means for securing said attachment to a penis.

2. The attachment of claim 1, wherein said means for securing comprise:

a generally dome-shaped bowl made of pliable sheet material having an arcuate upper surface and an arcuate lower surface, said lower surface being sized and dimensioned to conform to a tip section of a glans of said penis, said tip section encompassing a urethral orifice.

3. The attachment of claim 2, wherein said means for exposing comprise:

said bowl having an aperture penetrating through a central portion of said bowl and leading to said open end of said bladder.

4. The attachment of claim 3, wherein said means for securing further comprise:

an adhesive layer contacting an area of said lower surface surrounding said aperture.

5. The attachment of claim 4, wherein said retaining structure further comprises:

a generally dome shaped envelope having a circumferential edge connected to said upper surface of said bowl, and an upper arcuate portion through which said outlet extends.

6. The attachment of claim 5, wherein said outlet comprises a plurality of cuts through said envelope extending substantially radially from a substantially apical region of said envelope, thereby forming a plurality of flexible interrelating leaves biased in a closed position, said bias being weak enough to allow extrusion of said bladder through said outlet.

7. The attachment of claim 6, wherein said aperture has a first diameter larger than a widest dimension of said urethral orifice.

8. The attachment of claim 7, wherein said pliable sheet material is selected from the group consisting of latex rubber, synthetic rubber and plastic.

9. The attachment of claim 8, wherein said adhesive layer comprises a pressure-sensitive medical grade adhesive.

10. The attachment of claim 9, wherein said opening of said bladder terminates in a substantially circular flange, said flange being bonded to said upper surface.

11. The attachment of claim 9, wherein said bladder and said bowl are manufactured from a single piece of said pliable sheet material.

12. The attachment of claim 9, which further comprises a removable protective cover contacting said adhesive layer.

13. A contraceptive, prophylactic penile cap which comprises:

a bowl made of pliable sheet material shaped and dimensioned to cup a portion of a tumescent penile glans, said portion including a urethral orifice, said bowl having a substantially apical aperture;

a collapsed bladder mounted above said bowl having a single opening in communication with said aperture;

an envelope surrounding said collapsed bladder and having a circumferential edge attached to said bowl, and an expandable outlet sized and shaped to allow expansion of said bladder therethrough; and means for securing said bowl to said portion of said glans.

* * * * *